United States Patent [19]

Salek et al.

[11] Patent Number: 5,144,088

[45] Date of Patent: * Sep. 1, 1992

[54] MANUFACTURE OF NEOPENTYL GLYCOL (I)

[75] Inventors: Jeffrey S. Salek, Oakdale Boro; Joseph Pugach, Monroeville Boro, both of Pa.

[73] Assignee: Aristech Chemical Corporation, Pittsburgh, Pa.

[*] Notice: The portion of the term of this patent subsequent to Sep. 8, 2009 has been disclaimed.

[21] Appl. No.: 691,927

[22] Filed: Apr. 26, 1991

[51] Int. Cl.$^5$ .................... C07C 45/45; C07C 29/14; C07C 31/20
[52] U.S. Cl. .................... 568/457; 568/463; 568/464; 568/458; 568/853; 568/881; 568/880
[58] Field of Search ............... 568/853, 881, 457, 458, 568/463, 464, 880

[56] References Cited

U.S. PATENT DOCUMENTS

| | | | |
|---|---|---|---|
| 2,135,063 | 11/1938 | Walker et al. | 260/635 |
| 2,317,456 | 4/1943 | Hanford et al. | 260/602 |
| 2,778,858 | 1/1957 | Meinhofer | 260/635 |
| 2,786,083 | 3/1957 | Wyler | 260/635 |
| 2,811,562 | 10/1957 | Hagemeyer, Jr. | 260/602 |
| 3,340,312 | 9/1967 | Duke, Jr. et al. | 260/635 |
| 3,504,042 | 3/1970 | Shimono et al. | 260/635 |
| 3,808,280 | 4/1974 | Merger et al. | 260/635 A |
| 3,876,706 | 4/1975 | Levanevsky et al. | 260/602 |
| 3,920,760 | 11/1975 | Heinz | 568/464 |
| 3,935,274 | 1/1976 | Jacobsen et al. | 260/602 |
| 3,975,450 | 8/1976 | Palmer et al. | 260/635 P |
| 4,219,508 | 8/1980 | Wagner | 568/463 |
| 4,851,592 | 7/1989 | Morris | 568/853 |
| 4,855,515 | 8/1989 | Morris et al. | 568/862 |
| 4,945,184 | 7/1990 | Pugach et al. | 568/313 |

FOREIGN PATENT DOCUMENTS 1017618 1/1966 United Kingdom .

Primary Examiner—Marianne M. Cintins
Assistant Examiner—Rebecca Cook
Attorney, Agent, or Firm—William L. Krayer

[57] ABSTRACT

Neopentyl glycol is made by reacting isobutyraldehyde with paraformaldehyde in the presence of a tertiary amine and one or more oxides of elements of Groups IB, IVA, IVB, VA, VB, VIB and VIII of the periodic table; then hydrogenating the resulting hydroxypivaldehyde-containing product.

14 Claims, No Drawings

MANUFACTURE OF NEOPENTYL GLYCOL (I)

TECHNICAL FIELD

This invention relates to the manufacture of neopentyl glycol. In particular it relates to the manufacture of neopentyl glycol by reacting isobutyraldehyde with paraformaldehyde in the presence of a catalyst comprising one or more oxides of elements of Groups IB, IVA, IVB, VA, VB, VIB and VIII of the periodic table and triethylamine or other lower alkyl tertiary amine, and hydrogenating the reaction product which includes hydroxypivaldehyde dimer.

BACKGROUND ART

Prior to this invention, it has been known to make neopentyl glycol (2,2 dimethyl-1,3-dihydroxypropane, also known herein as NPG) by reacting formaldehyde with isobutyraldehyde and hydrogenating the resulting hydroxypivaldehyde (HPA). See U.S. Pat. No. 4,855,515, for example, which recites the historical development of the reaction and emphasizes the use of a particular catalyst in the hydrogenation step. U.S. Pat. No. 3,808,280 discloses the use of triethylamine as a catalyst for the (aqueous) formaldehyde/isobutyraldehyde reaction.

Each of the above references employs formaldehyde in the form of aqueous formaldehyde.

Paraformaldehyde is used by Snam S.p.A. in UK Patent 1,017,618 to react with isobutyraldehyde in the presence of a tertiary amine to produce a reaction product containing apparently predominantly hydroxypivaldehyde which may be hydrogenated to neopentyl glycol. No reference to our knowledge teaches the use of one or more oxides of elements of Groups IB, IVA, IVB, VA, VB, VIB and VIII of the periodic table and paraformaldehyde with the accompanying advantages as explained below. Nor are we are of the use of metal oxide as a catalyst in such a reaction.

SUMMARY OF THE INVENTION

The present invention is a method of making hydroxypivaldehyde (HPA), and particularly its dimers, 2-[1,1-dimethyl-2-hydroxy-methyl]-5,5-dimethyl-4-hydroxy-1,3-dioxane and subsequently neopentyl glycol (NPG), by reacting isobutyraldehyde (IBAL or 2-methylpropanal) with paraformaldehyde in the presence of a tertiary amine catalyst, preferably triethylamine, and one or more oxides of elements of Groups IB, IVA, IVB, VA, VB, VIB and VIII of the periodic table (Chemical Rubber Company Handbook) to obtain HPA and HPA dimer, and hydrogenating the HPA and its dimer to obtain NPG. The HPA may be isolated in the form of the HPA dimer, which is a white solid:

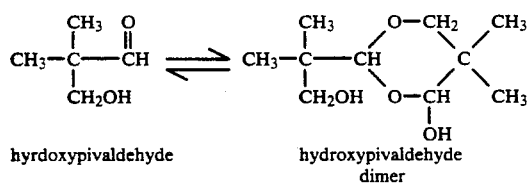

hyrdoxypivaldehyde     hydroxypivaldehyde dimer

The HPA is obtained at a faster rate and with a higher yield then in the presence of the metal oxide. Whether or not the HPA or its dimer is isolated and/or purified, they are conveniently hydrogenated a methanol solution, and in the presence of a copper chromite catalyst, for example, to obtain the desired neopentyl glycol. The HPA dimer hydrogenates as readily as HPA itself.

A specific reaction may be described as follows: The reaction is performed in a reflux apparatus wherein one equivalent of isobutylraldehyde, 0.01 equivalent of titanium dioxide, and about 0.04 to 0.05 equivalent of triethylamine have been placed under an inert atmosphere. Stir at the reflux temperature of isobutyraldehyde (about 63°–64° C.) until the isobutyraldehyde no longer refluxes, i.e. is consumed. The clear faintly yellow molten liquid obtained is decanted—or filtered from the titanium dioxide and gradually cooled to room temperature. Hydroxypivaldehyde dimer can be obtained by allowing it to precipitate and then washing to remove the amine catalyst, or crystallizing from a methanol solution. The HPA dimer, together with any residual HPA, is hydrogenated in any conventional (convenient) manner such as by passing a methanol solution over a copper chromite catalyst at about 150° C. and about 2000 psi, to obtain the neopentyl glycol, which is finally purified by recrystallization and/or distillation.

More generally, with one equivalent of isobutyraldehyde we may place in a reaction vessel from about 2 to about 0.1 equivalent of paraformaldehyde, about 0.001 to about 0.1 (preferably about 0.005 to about 0.05) equivalent of one or more oxides of elements of Groups IB, IVA, IVB, VA, VB, VIB and VIII of the periodic table and about 0.01 to about 0.1 (preferably 0.02 to about 0.08) equivalent of a tertiary amine. The reaction mixture is stirred under an argon purge until reflux of the isobutyraldehyde ceases. The resulting hydroxypivaldehyde and its dimer may be hydrogenated without without further purification.

As is known in the art, if the amine chosen has a boiling point lower than the boiling point (reflux temperature) of isobutyraldehyde, pressure may be used.

Our invention provides a process in which water is not utilized and is therefore relatively easier to perform since it does not require the separation and/or disposal of water; the process is also considerably more efficient than prior art processes, since the HPA product can be used directly, i.e. without an arduous separation or purification process, for the hydrogenation step to NPG. However, if the product is to be stored, it is interesting to note that HPA dimer can be exposed to air indefinitely, as opposed to the monmer, which oxidizes rapidly to hydroxypivalic acid. The process is also more efficient in that fewer by-products are made, a high yield is obtained at a fast rate, and indeed one need not be concerned with the complications of by-products. Under properly controlled conditions, paraformaldehyde is easier and safer to store than aqueous formaldehyde.

The metal oxide catalyst can be removed from the HPA reaction product before it is hydrogenated, by filtration or by any convenient means for recycling. The reaction may also be performed over a bed of catalyst.

We may use various tertiary amines. Specifically, we may use as catalysts any tertiary amines of the general formula $R^1R^2R^3N$ wherein $R^1$, $R^2$, and $R^3$ are independently selected from alkyl and aryl groups of the general formula $C_1$-$C_{15}$ and $R^1$ and $R^2$ may form a substituted or unsubstituted cyclic group having from about 5 to about 15 carbon atoms.

DETAILED DESCRIPTION OF THE INVENTION

Following are several examples of the invention:

EXAMPLE 1

In this experiment, isobutyraldehyde was converted to hydroxypivaldehyde dimer.

Isobutyraldehyde (554.7 mmol), triethylamine (27.7 mmol), paraformaldehyde (527.0 mmol) and niobium oxide (5.6 mmol) were charged into a 250 ml rbf containing a magnetic stirbar and fitted with a reflux condenser. The rbf portion of the apparatus was submerged in a 80° C. oil bath with magnetic stirring. The reaction was continued under an argon purge until the isobutyraldehyde no longer refluxed (generally about 1 to 3 hours) at which point the molten solution was allowed to slowly cool to room temperature. After the niobium oxide settled, the reaction mixture was decanted off and was allowed to stand at room temperature for about 2 days. Solidification occurred (normally about 1 to about 3 days is required); the solid was recovered by suction filtration, pulverization, and washing with hexane. Hydroxypivaldehyde dimer (450 mmol) was observed as a white powder (m.p. 88°–90° C.) giving an isolated yield of 85% based on reacted paraformaldehyde; the HPA dimer was 92% pure by G.C. analysis. Higher purity dimer was obtained by recrystallization from methanol, and gave material melting at 106°–108° C.

EXAMPLE 2

Example 1 was repeated without niobium oxide, yielding 403 mmol of hydroxypivaldehyde dimer with a melting point of 84°–86° C. in 76% isolated yield based on reacted paraformaldehyde at 82% purity by G.C. analysis.

EXAMPLE 3

Hydroxypivaldehyde dimer made by the specific reaction described in the Summary of the Invention was dissolved in methanol to give 15.2% by weight solution. The solution was hydrogenated in an autoclave reaction over barium activated copper chromite at 150° C. and 200 lb hydrogen pressure giving quantitative conversion of hydroxypivaldehyde to neopentyl glycol, i.e., >99% purity was obtained as measured by gas chromatography without any special treatment such as the commonly used caustic purification treatment.

Table I recites the results of experiments utilizing

| Reagent | Equivalents |
| --- | --- |
| IBAL | 1.00 |
| Paraformaldehyde | 1.00 |
| Triethylamine | 0.050 |
| Metal oxide | 0.010 |

The reactions were terminated 1 hour after the IBAL stopped refluxing and then analyzed by G.C. Everything else was done as similarly as possible so that the effect of the metal oxides could be compared. HPA selectivity was calculated as the monomer.

TABLE I

| Co-Catalyst | % IBAL Conv. | % HPA Sel. | % "44G" Sel.* | Reaction Time (h) | Comments |
| --- | --- | --- | --- | --- | --- |
| 1. None | 92 | 92 | 3.7 | 2.42 | Control |
| 2. Nb$_2$O$_5$ | 97 | 96 | 1.3 | 2.08 | |
| 3. ZrO$_2$ | 98 | 97 | 1.0 | 2.00 | |
| 4. MnO$_2$ | 97 | 90 | 7.3 | 1.92 | |
| 5. As$_2$O$_3$ | 97 | 97 | 1.3 | 2.00 | |
| 6. CuO | 97 | 96 | 2.4 | 1.92 | |
| 7. TiO$_2$ | 99 | 98 | 0.3 | 1.17 | |
| 8. CdO | 97 | 66 | 29.0 | 1.08 | |
| 9. CeO$_2$ | 97 | 94 | 0.6 | 1.33 | |
| 10. NiO | 96 | 91 | 7.0 | 1.58 | |
| 11. Sm$_2$O$_3$ | 99 | 91 | 1.1 | 2.00 | |
| 12. Silica Gel | 97 | 97 | 1.7 | 2.50 | |
| 13. Cr$_2$O$_3$ | 99 | 95 | 2.7 | 1.58 | |
| 14. Bi$_2$O$_3$ | 99 | 96 | 2.1 | 2.50 | |
| 15. Y$_2$O$_3$ | 95 | 58 | 31.5 | 1.75 | |

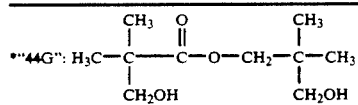

*"44G": 
$$H_3C-\underset{\underset{CH_2OH}{|}}{\overset{\overset{CH_3}{|}}{C}}-\overset{O}{\overset{\|}{C}}-O-CH_2-\underset{\underset{CH_2OH}{|}}{\overset{\overset{CH_3}{|}}{C}}-CH_3$$

The hydroxypivaldehyde may be hydrogenated to neopentyl glycol using known chemical methods such as sodium borohydride reduction or catalytic techniques which involve conventional hydrogenation catalysts like copper chromite, nickel or alumina, or ruthenium on carbon.

For example, an aldol reaction was performed using a stoichiometric amount of isobutyraldehyde and paraformaldehyde in the presence of 5 equivalent percent of triethylamine and 1 equivalent percent Nb$_2$O$_5$. The stirred mixture was heated under an argon purge until a moderate isobutyraldehyde reflux was achieved. The reaction was terminated when isobutyraldehyde reflux ceased. The reaction solution was cooled to approximately 50° C. and filtered to remove the Nb$_2$O$_5$. The clear, faintly yellow filtrate was diluted to make a 15 wt. % solution in methanol and was then transferred into a 2 liter autoclave reactor. Copper chromite was added (3 wt. % based on aldol charge). Batch hydrogenation at 130° C. for two hours at 3000 p.s.i.g. H$_2$ followed by a reduced pressure, 10-tray fractional distillation of the hydrogenation effluent gave neopentyl glycol product in ~90% yield at >99.5% purity.

We claim:

1. Method of making hydroxypivaldehyde and its dimer comprising reacting paraformaldehyde with isobutyraldehyde in the presence of a catalyst comprising a tertiary amine and one or more oxides of elements of Groups IB, IVA, IVB, VA, VB, VIB and VIII of the periodic table.

2. Method of making neopentyl glycol comprising reacting paraformaldehyde with isobutyraldehyde in the presence of a catalyst comprising a tertiary amine and one or more oxides of elements of Groups IB, IVA, IVB, VA, VB, VIB and VIII of the periodic table to obtain monomeric and dimeric hydroxypivaldehyde, and hydrogenating the monomeric and dimeric hydroxypivaldehyde.

3. Method of claim 1 wherein the tertiary amine is triethylamine.

4. Method of claim 2 wherein the tertiary amine is triethylamine.

5. Method of claim 1 wherein the ratio of paraformaldehyde to isobutyraldehyde is about 1:2 to about 10:1.

6. Method of claim 1 wherein the reaction is conducted under isobutyraldehyde reflux conditions.

7. Method of claim 1 followed by recovering a reaction product, and wherein dimeric hydroxypivaldehyde is recovered from the reaction product by crystallization from a solvent.

8. Method of claim 1 followed by recovering a reaction product, and wherein dimeric hydroxypivaldehyde is recovered from the reaction product by crystallization from a solvent.

9. Method of claim 2 including the step of recovering the oxide prior to hydrogenation of the hydroxypivaldehyde.

10. Method of claim 1 wherein the amine has the formula $R^1R^2R^3N$ where $R^1$, $R^2$, and $R^3$ are independently selected from alkyl and aryl groups of the general formula $C_1$–$C_{15}$ and $R^1$ and $R^2$ may form a substituted or unsubstituted cyclic group having from about 5 to about 15 carbon atoms.

11. Method of claim 1 wherein the oxide is titanium oxide.

12. Method of claim 2 wherein the oxide is titanium oxide.

13. Method of claim 1 wherein the oxide is chromium oxide.

14. Method of claim 2 wherein the oxide is chromium oxide.

* * * * *

UNITED STATES PATENT AND TRADEMARK OFFICE
CERTIFICATE OF CORRECTION

PATENT NO. : 5,144,088

DATED : September 1, 1992

INVENTOR(S) : Jeffrey S. Salek and Joseph Pugach

It is certified that error appears in the above-identified patent and that said Letters Patent is hereby corrected as shown below:

Column 1, line 43, change "dimers" to -- dimer --;

line 65, change "presence" to -- absence --;

line 67, after "hydrogenated" insert -- in --.

Column 2, line 5, change "isobutylraldehyde" to -- isobutyraldehyde --;

same line, after "isobutylraldehyde," insert -- one equivalent of paraformaldehyde, --;

line 35, change "out" to -- or --;

line 64, change "wherein" to -- where --.

Column 3, line 42, change "reaction" to -- reactor --;

line 44, change "200" to -- 2000 --.

Column 4, line 26, after "nickel" change "or" to -- on -- ;

line 43, change "hydrogenation" to -- hydrogenated --.

Column 5, lines 3 and 4, claim 7, delete "crystallization from a solvent" and substitute -- precipitation --.

UNITED STATES PATENT AND TRADEMARK OFFICE
CERTIFICATE OF CORRECTION

PATENT NO. : 5,144,088
DATED : September 1, 1992
INVENTOR(S) : Jeffrey S. Salek and Joseph Pugach It is certified that error appears in the above-indentified patent and that said Letters Patent is hereby corrected as shown below:

Column 6, line 6, claim 11, change "oxide" to --dioxide--;

line 8, claim 12, change "oxide" to --dioxide--.

Signed and Sealed this

Fifth Day of October, 1993

Attest:

BRUCE LEHMAN

Attesting Officer

Commissioner of Patents and Trademarks